United States Patent [19]

Caufield

[11] Patent Number: 5,102,876
[45] Date of Patent: Apr. 7, 1992

[54] REDUCTION PRODUCTS OF RAPAMYCIN

[75] Inventor: Craig E. Caufield, Plainsboro, N.J.

[73] Assignee: American Home Products Corporation, New York, N.Y.

[21] Appl. No.: 696,692

[22] Filed: May 7, 1991

[51] Int. Cl.[5] .................. A61K 31/395; C01D 491/00
[52] U.S. Cl. .................................. 514/183; 514/321; 540/456
[58] Field of Search ................. 540/456; 514/183, 321

[56] References Cited

U.S. PATENT DOCUMENTS

| | | | |
|---|---|---|---|
| 3,929,992 | 12/1975 | Seghal et al. | 122/122 |
| 3,993,749 | 11/1976 | Seghal et al. | 424/122 |
| 4,316,885 | 2/1982 | Rakhit | 424/122 |
| 4,401,653 | 4/1983 | Eng | 424/114 |
| 4,650,803 | 3/1987 | Stella et al. | 546/90 |
| 4,885,171 | 12/1989 | Surendra et al. | 424/122 |

OTHER PUBLICATIONS

J. Antibiot. 28, 721–732, (1975).
J. Antibiot. 31, 539–545 (1978).
FASEB 3, 3411, 5256 (1989).
Lancet, pp. 1183–1185 (1978).
J. Am. Chem. Soc. 103, pp. 3215–3217 (1981).
Immunology, C. V. Moseby Co., pp. 12.8–12.11 (1989).

Primary Examiner—Robert T. Bond
Attorney, Agent, or Firm—Robert F. Boswell, Jr.

[57] ABSTRACT

Reduction of rapamycin with DIBAL furnishes either the 15-hydroxyrapamycin or 15,27-bis(hydroxy)rapamycin, depending upon the reaction conditions, having the general structure

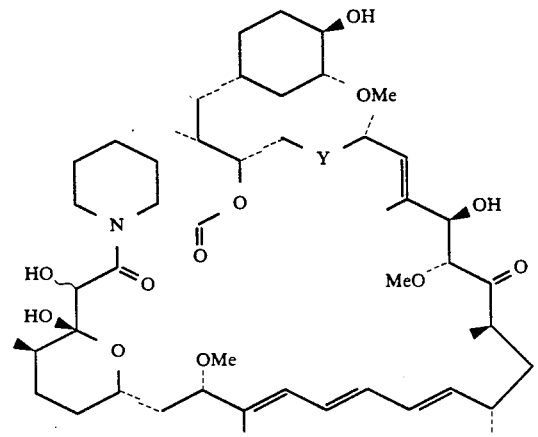

where Y is —CO— —CH(OH)—.

The compounds of this invention are useful in treating transplant rejection, host vs. graft disease, autoimmune diseases, diseases of inflammation, and fungal infections.

7 Claims, No Drawings

REDUCTION PRODUCTS OF RAPAMYCIN

BACKGROUND OF THE INVENTION

This invention relates to compounds of formula I or pharmaceutically acceptable salts thereof, which possess immunosuppressive and/or antifungal and/or antitumor and/or antiinflammatory activity in vivo and/or inhibit thymocyte proliferation in vitro and are therefore useful in the treatment of transplantation rejection, autoimmune diseases (i.e. lupus, rheumatoid arthritis, diabetes mellitus, multiple sclerosis), Candida albicans infections, and diseases of inflammation.

Rapamycin is a macrocyclic triene antibiotic produced by Streptomyces hygroscopicus, which was found to have antifungal activity, particularly against Candida albicans, both in vitro and in vivo [C. Vezina et al., J. Antibiot. 28, 721 (1975); S. N. Seghal et al., J. Antibiot. 28, 727 (1975); H. A. Baker et al., J. Antibiot. 31, 539 (1978); U.S. Pat. Nos. 3,929,992; and 3,993,749].

Rapamycin alone (U.S. Pat. No. 4,885,171) or in combination with picibanil (U.S. Pat. No. 4,401,653) has been shown to have antitumor activity. R. Martel et al. [Can. J. Physiol. Pharmacol. 55, 48 (1977)] disclosed that rapamycin is effective in the experimental allergic encephalomyelitis model, a model for multiple sclerosis; in the adjuvant arthritis model, a model for rheumatoid arthritis; and effectively inhibited the formation of IgE-like antibodies.

The immunosuppressive effects of rapamycin have been disclosed in FASEB 3, 3411 (1989). Rapamycin has been shown to be effective in inhibiting transplant rejection (U.S. patent application Ser. No. 362,544 filed June 6, 1989). Cyclosporin A and FK-506, other macrocyclic molecules, also have been shown to be effective as immunosuppressive agents, therefore useful in preventing transplant rejection [FASEB 3, 3411 (1989); FASEB 3, 5256 (1989); and R. Y. Calne et al., Lancet 1183 (1978)].

SUMMARY OF THE INVENTION

This invention provides derivatives of rapamycin which are useful as immunosuppressive, antiinflammatory, antifungal, and antitumor agents. The invention compounds thus are useful in the treatment of transplant rejection, autoimmune diseases (i.e., lupus, rheumatoid arthritis, diabetes mellitus, multiple sclerosis), Candida albicans infections, and diseases of inflammation.

The compounds of this invention are represented by Formula I below:

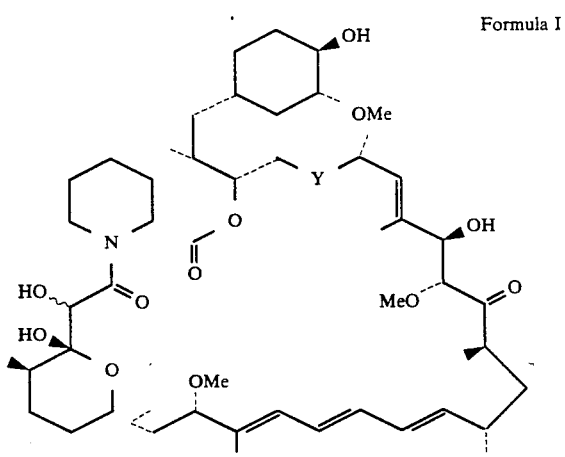

Formula I

Under Formula I Y is —CO— or —CH(OH)—. Formula I also encompasses the pharmaceutically acceptable salts which may be formed from inorganic cations such as sodium, potassium and the like.

DETAILED DESCRIPTION OF THE INVENTION

The Formula I compounds of the present invention are prepared by reacting rapamycin with diisobutylaluminum hydride (DIBAL) or a similar reagent as outlined in schemes A and B below when only the pertinent portion of the molecular structure are shown.

Scheme A. Reduction of rapamycin at position 15

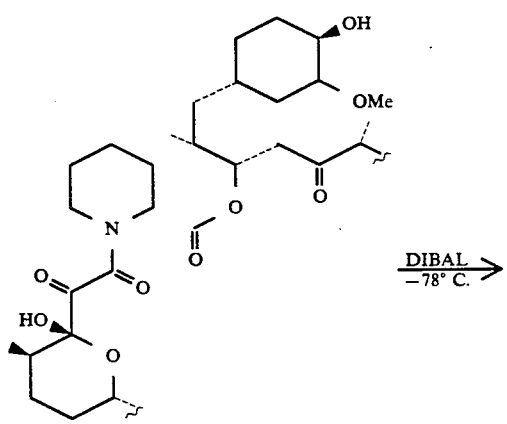

-continued
Scheme A. Reduction of rapamycin at position 15

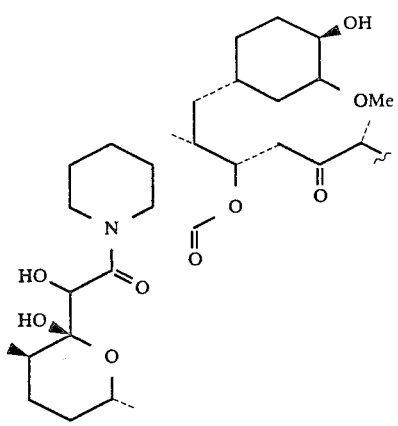

Reaction of rapamycin with DIBAL at −78° C. in anhydrous tetrahydrofuran (THF) results in the keto group at position 15 being reduced.

When the reaction mixture is allowed to proceed at −20° C. following addition of DIBAL at −78° C., reduction of the keto groups at positions 15 and 27 occurs giving the 15, 27 diol as shown in Scheme B.

Scheme B. Reduction of Rapamycin at positions 15 and 27

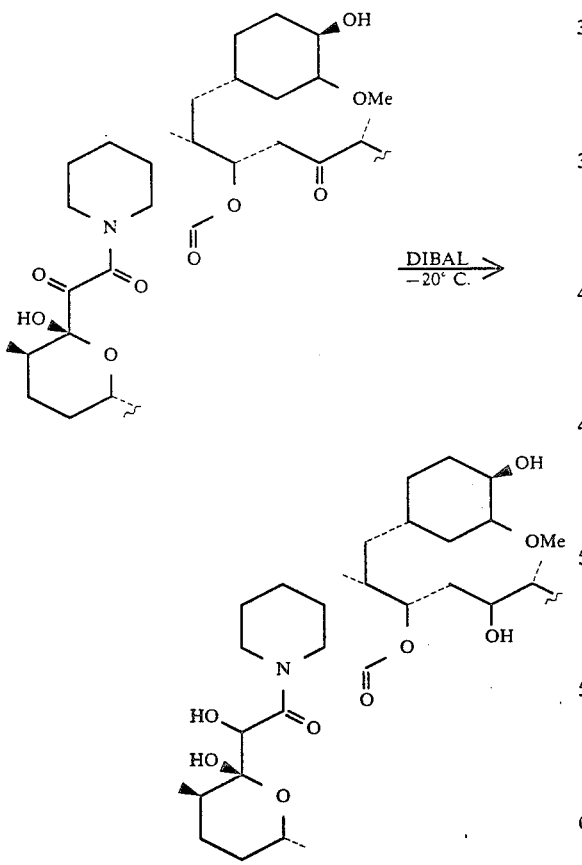

Diastereomers obtained in Scheme B are separated by chromatographic procedures, i.e., preparative high pressure liquid chromatography.

Immunosuppressive activity was evaluated in an in vitro standard pharmacological test procedure to measure lymphocyte proliferation (LAF) and in two in vivo standard pharmacological test procedures. The first in vivo procedure was a popliteal lymph node (PLN) test procedure which measured the effect of compounds of this invention on a mixed lymphocyte reaction and the second in vivo procedure evaluated the survival time of a pinch skin graft.

The comitogen-induced thymocyte proliferation procedure (LAF) was used as an in vitro measure of the immunosuppressive effects of representative compounds. Briefly, cells from the thymus of normal BALB/c mice are cultured for 72 hours with PHA and IL-1 and pulsed with tritiated thymidine during the last six hours. Cells are cultured with and without various concentrations of rapamycin, cyclosporin A, or test compound. Cells are harvested and incorporated; radioactivity is determined. Inhibition of lymphoproliferation is assessed in percent change in counts per minute from non-drug treated controls. The results are expressed by the following ratio, or as the percent inhibition of lymphoproliferation of 1 μM.

$$\frac{^3\text{H-control thymus cells} - {^3\text{H-rapamycin-treated thymus cells}}}{^3\text{H-control thymus cells} - {^3\text{H-test compound-treated cells}}}$$

A mixed lymphocyte reaction (MLR) occurs when lymphoid cells from genetically distinct animals are combined in tissue culture. Each stimulates the other to undergo blast transformation which results in increased DNA synthesis that can be quantified by the incorporation of tritiated thymidine. Since stimulating a MLR is a function of disparity at Major Histocompatibility antigens, an in vivo popliteal lymph node (PLN) test procedure closely correlates to host vs. graft disease. Briefly, irradiated spleen cells from BALB/c donors are injected into the right hind foot pad of recipient C3H mice. The drug is given daily, p.o. from Day 0 to Day 4. On Day 3 and Day 4, tritiated thymidine is given i.p., b.i.d. On Day 5, the hind popliteal lymph nodes are removed and dissolved, and radioactivity counted. The corresponding left PLN serves as the control for the PLN from the injected hind foot. Percent suppression is calculated using the non-drug treated animals as allogenic control. Rapamycin at a dose of 6 mg/kg, p.o. gave 86% suppression, whereas cyclosporin A at the same dose gave 43% suppression. Results are expressed by the following ratio:

$$\frac{^3\text{H-PLN cells control C3H mouse} - {^3\text{H-PLN cells rapamycin-treated C3H mouse}}}{^3\text{H-PLN cells control C3H mouse} - {^3\text{H-PLN cells test compound-treated C3H mouse}}}$$

The second in vivo test procedure is designed to determine the survival time of pinch skin graft from male DBA/2 donors transplanted to male BALB/c recipients. The method is adapted from Billingham R. E. and Medawar P. B., J. Exp. Biol. 28: 385–402, (1951). Briefly, a pinch skin graft from the donor is grafted on the dorsum of the recipient as a homograft, and an autograft is used as control in the same region. The recipients are treated with either varying concentrations of cyclosporin A as test control or the test compound, intraperitoneally. Untreated recipients serve as rejection control. The graft is monitored daily and observations are recorded until the graft becomes dry and forms a blackened scab. This is considered as the rejection day. The mean graft survival time (number of days±S.D.) of the drug treatment group is compared with the control group.

The following table summarizes the results of the compounds of this invention in these three standard test procedures.

TABLE 1

| Compound | LAF* | PLN* | Skin Graft (days + SD) |
|---|---|---|---|
| Example 1 | 0.58 | −2.47 po, −0.07 ip | 9.8 ± 1.0 |
| Example 2 | 0.67 | — | 9.2 ± 0.41 |
| Example 3 | 0.84 | 0.92 ip | 9.5 ± 5.5 |

*Activity of analog at 100 nM as compared with rapamycin

The results of these standard pharmacological test procedures demonstrate immunosuppressive activity both in vitro and in vivo for the compounds of this invention. Positive ratios in the LAF and PLN test procedures indicate suppression of T cell proliferation. As transplanted pinch skin grafts are typically rejected with 6-7 days without the use of an immunosuppressive agent, the increased survival time of the skin graft when treated with the compounds of this invention further demonstrates their utility as immunosuppressive agents.

Antifungal activity of the compounds of this invention was measured against 5 strains of *Candida albicans* using a plate test procedure for measurement of inhibition. The following represents the typical procedure used. The compound to be tested was placed on sterile dried ¼" plate disks, and allowed to dry. Agar plates were seeded with fungi and allowed to solidify. The impregnated disks were placed on the seeded Agar surface and incubated for the time required for the particular culture. Results are expressed in MIC (μg/ml) to inhibit growth. The results of this test procedure showed that the compounds of this invention have antifungal activity.

The compound of Example 1 had the following minimal inhibitory concentrations (50%) against 5 strains of *Candida albicans*.

| | Strains of *Candida albicans* | | | | |
|---|---|---|---|---|---|
| Compound | ATCC 10231 | ATCC 38246 | ATCC 38247 | ATCC 38248 | 3669 |
| Example 1 | 0.025 | 0.2 | 0.025 | 0.05 | 0.2 |
| Rapamycin | 0.003 | 0.025 | 0.003 | 0.006 | 0.025 |

Based on the results of these standard pharmacological test procedures, the compounds are useful in the treatment of transplantation rejection such as, heart, kidney, liver, bone marrow, and skin transplants; autoimmune diseases such as, lupus, rheumatoid arthritis, diabetes mellitus, myasthenia gravis, and multiple sclerosis; and diseases of inflammation such as, psoriasis, dermatitis, eczema, seborrhea, inflammatory bowel disease; and fungal infections.

The compounds may be administered neat or with a pharmaceutical carrier to a mammal in need thereof. The pharmaceutical carrier may be solid or liquid.

A solid carrier can include one or more substances which may also act as flavoring agents, lubricants, solubilizers, suspending agents, fillers, glidants, compression aids, binders or tablet-disintegrating agents; it can also be an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers are used in preparing solutions, suspensions, emulsions, syrups, elixirs and pressurized compositions. The active ingredient can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (partially containing additives as above, e.g. cellulose derivatives, preferably sodium carboxymethyl cellulose solution), alcohols (including monohydric alcohols and polyhydric alcohols, e.g. glycols) and their derivatives, and oils (e.g. fractionated coconut oil and arachis oil). For parenteral administration, the carrier can also be an oily ester such as ethyl oleate and isopropyl myristate. Sterile liquid carriers are useful in sterile liquid form compositions for parenteral administration. The liquid carrier for pressurized compositions can be halogenated hydrocarbon or other pharmaceutically acceptable propellent.

Liquid pharmaceutical compositions which are sterile solutions or suspensions can be utilized by, for example, intramuscular, intraperitoneal or subcutaneous injection. Sterile solutions can also be administered intravenously. The compound can also be administered orally either in liquid or solid composition form.

Preferably, the pharmaceutical composition is in unit dosage form, e.g. as tablets or capsules. In such form, the composition is sub-divided in unit dose containing appropriate quantities of the active ingredient; the unit dosage forms can be packaged compositions, for example, packeted powders, vials, ampoules, prefilled syringes or sachets containing liquids. The unit dosage form can be, for example, a capsule or tablet itself, or it can be the appropriate number of any such compositions in package form. The dosage to be used in the treatment must be subjectively determined by the attending physician.

In addition, the compounds of this invention may be employed as a solution, cream, or lotion by formulation with pharmaceutically acceptable vehicles containing 0.1–0.5 percent, preferably 2%, of active compound which may be administered to a fungally affected area.

The following examples illustrate the preparation of the compounds of this invention.

EXAMPLE 1

15-Deoxo-15-hydroxyrapamycin

To a solution of 750 mg (821 μmol) of rapamycin in 15 mL of dry THF was added dropwise at −78° C., 3.6 mL (3.6 mmol) of a 1.0M solution of DIBAL in hexanes. After 1 h, the reaction was worked up by adding 1.0N HCl to dissolve the aluminum salts. The aqueous solution was extracted three times with ethyl acetate, the combined organics washed with brine, dried over sodium sulfate, and concentrated in vacuo to give a colorless transparent solid. The residue was recrystallized from diisopropyl ether/hexane to give after filtration, 275 mg (37%) of 15-deoxo-15-hydroxyrapamycin, mp 118°–122° C.

The spectral data follow: $^1$H NMR (CDCl$_3$, 400 MHz) δ4.42 (d, 1H, —OH), 4.17 (bs, 1H, anomeric OH), 3.40 (s, 3H, OCH$_3$), 3.39 (s, 3H, OCH$_3$), 3.14 (s, 3H, OCH$_3$), 1.75 (s, 3H, CH$_3$C=C), 1.60 (s, 3H, CH$_3$C=C); $^{13}$C NMR (CDCl$_3$, 100 MHz) δ216.0, 209.0, 174.5, 169.9; IR (KBr) 3440, 2940, 2860, 1740, 1720, 1630, 1450, 1380, 1195, 1090 cm$^{-1}$; MS (neg. ion FAB) 914 (M—H), 592, 339, 184, 168 (100).

Analysis Calcd. for C$_{51}$H$_{81}$NO$_{13}$: C, 66.86; H, 8.91; N, 1.53. Found: C, 66.46; H, 9.03; N, 1.36.

EXAMPLE 2

15,27-Bis(deoxo)-15,27-bis(hydroxy)rapamycin

To a solution of 1.43 g (1.56 mmol) of rapamycin in 20 mL of dry THF at −78° C. was added dropwise 6.87 mL (6.87 mmol) of a 1.0M solution of DIBAL in toluene. The reaction was slowly warmed to −20° over a 4 h period and then quenched by stirring over 1.0N HCl for 20 min. The reaction mixture was extracted three times with ethyl acetate, the organic layers combined, washed with brine, dried over sodium sulfate, filtered, and concentrated in vacuo to give a foamy solid. The residue was purified via HPLC chromatography (2 in Dynamax silica column, 100% ethyl acetate, 35 mL/min) gave 90 mg (6%) of 15,27-bis(deoxy)-15,27-bis(hydroxy)rapamycin.

The spectral data follow: $^1$H NMR (CDCl$_3$, 400 MHz) δ4.35 (m, 1H, —OH), 4.17 (bs, 1H, anomeric OH), 3.39 (s, 3H, OCH$_3$), 3.33 (s, 3H, OCH$_3$), 3.12 (s, 3H, OCH$_3$), 1.71 (s, 3H, CH$_3$C=C), 1.58 (s, 3H, CH$_3$C=C); IR (KBr) 3435, 2930, 2870, 1740, 1720, 1640, 1450, 1380, 1195, 1090 cm$^{-1}$; MS (neg. ion FAB) 917 (M—).

Analysis Calcd. for C$_{51}$H$_{83}$NO$_{13}$.2H$_2$O: C, 64.19; H, 9.19; N, 1.47. Found: C, 64.07; H, 8.28; N, 1.62.

EXAMPLE 3

15,27-Bis(deoxo)-15,27-bis(hydroxy)rapamycin

Using the above procedure, also collected as a second fraction, 60 mg (4%) of 15,27-bis(deoxo)-15,27-bis(hydroxy)rapamycin.

The spectral data follow: $^1$H NMR (CDCl$_3$, 400 MHz) δ4.39 (m, 1H, —OH), 4.21 (m, 1H, anomeric OH), 3.41 (s, 3H, OCH$_3$), 3.40 (s, 3H, OCH$_3$), 3.15 (s, 3H, OCH$_3$), 1.73 (s, 3H, CH$_3$C=C), 1.60 (s, 3H, CH$_3$C=C); IR (KBr) 3440, 2930, 2880, 1740, 1720, 1640, 1450, 1380, 1190, 1090 cm$^{-1}$; MS (neg. ion FAB) 917 (M—), 359, 168 (100).

Analysis Calcd. for C$_{51}$H$_{83}$NO$_{13}$.1.5H$_2$O: C, 64.80; H, 9.17; N, 1.48. Found: C, 64.69; H, 8.86; N, 1.59.

What is claimed is:

1. A compound of the formula

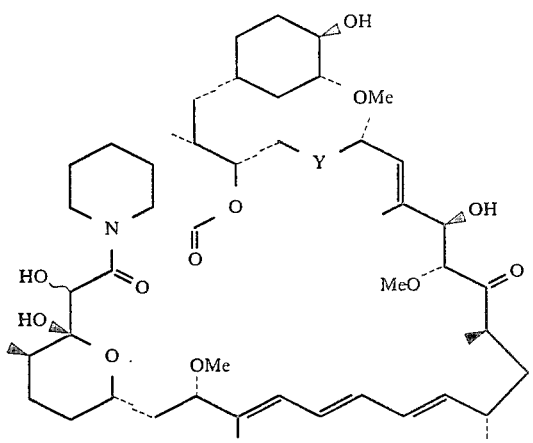

where Y is —CO— or —CH(OH)—, or a pharmaceutically acceptable salt thereof.

2. A compound according to claim 1 which is 15-deoxo-15-hydroxyrapamycin.

3. A compound according to claim 1 which is 15,27-bis(deoxo)-15,27-bis(hydroxy)rapamycin.

4. A method of treating transplantation rejection, host vs. graft disease, autoimmune diseases, and diseases of inflammation in a mammal by administering thereto an effective amount of a compound having the formula

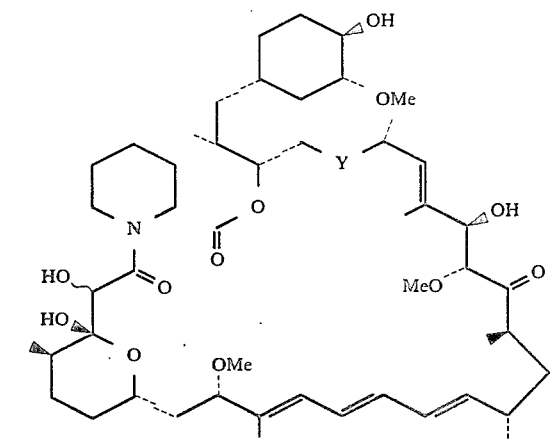

where Y is —CO— or —CH(OH)—, or a pharmaceutically acceptable salt thereof.

5. A method of treating fungal infections in mammals by administering thereto an effective amount of a compound having the formula

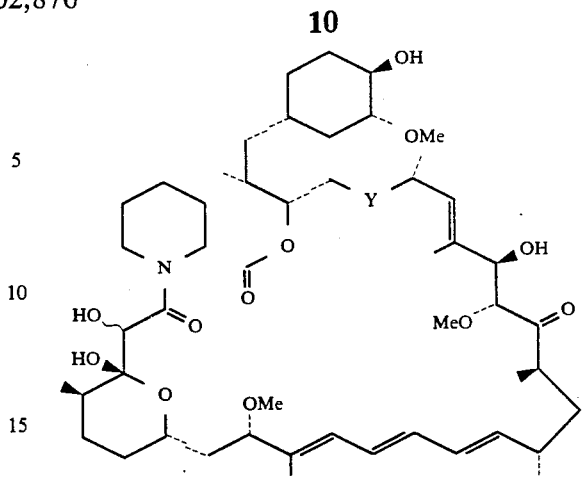

where Y is —CO— or —CH(OH)—, or a pharmaceutically acceptable salt thereof.

6. A pharmaceutical composition for treating transplantation rejection, host vs graft disease, autoimmune diseases, diseases of inflammation, and fungal infections comprising:
   a. a therapeutically effective amount of a compound according to claim 1 or a pharmaceutically acceptable salt thereof and
   b. a pharmaceutical carrier.

7. A pharmaceutical composition according to claim 6 in unit dosage form.

* * * * *